United States Patent [19]

Sack et al.

[11] Patent Number: 4,548,805

[45] Date of Patent: Oct. 22, 1985

[54] NON-INVASIVE TEST FOR GASTRIC ACID

[76] Inventors: David A. Sack, 2117 Bellvale Rd., Fallston, Md. 21047; Charles B. Stephensen, 3700 N. Charles St., Apt. #608, Baltimore, Md. 21218

[21] Appl. No.: 566,032

[22] Filed: Dec. 27, 1983

[51] Int. Cl.[4] .............................................. A61K 49/00
[52] U.S. Cl. ........................................ 424/9; 128/719; 128/730; 436/900
[58] Field of Search .......................... 424/9; 436/900; 128/719, 730, 205.28

[56] References Cited

U.S. PATENT DOCUMENTS 4,114,422  9/1978  Hutson .......................... 436/900 X
4,119,089  10/1978  Dreti et al. ..................... 436/900 X

FOREIGN PATENT DOCUMENTS 1467850  11/1968  Fed. Rep. of Germany .......... 424/9

OTHER PUBLICATIONS

Becker et al., Chemical Abstracts, 99(1983), #15960f.
Keyrilainen, Chemical Abstracts, 97(1982), #138045c.
Shibayama et al., Chemical Abstracts, 96(1982), #160067n.
Ivanou et al., Chemical Abstracts, 88(1978), 117370d.

*Primary Examiner*—Christine M. Nucker
*Attorney, Agent, or Firm*—Charles E. Temko

[57] ABSTRACT

A non-invasive method for determining gastric acidity in humans, using oral magnesium metal powder while measuring the hydrogen gas response in exhaled breath and belches. The magnesium reacts with hydrochloric acid in the stomach liberating hydrogen and the magnitude of the hydrogen released is correlated with the amount of gastric acid produced.

2 Claims, No Drawings

NON-INVASIVE TEST FOR GASTRIC ACID

BACKGROUND OF THE INVENTION

This invention relates generally to the field of medical diagnostics, and more particularly to a non-invasive test for gastric acid secretion based upon the reaction of an orally administered substance which reacts with gastric acid, and in which hydrogen gas thus evolved is detected in exhaled air and belches and quantitatively related to the amount of acid in the stomach.

Gastric acid secretion is important in several disease conditions. Elevated basal levels are seen with the Zollinger-Ellison syndrome and decreased levels are seen in pernicious anemia and in some patients with gastric carcinoma. Hypochlorhydria predisposes to infectious diarrhea (1), (2), (3), (4), especially those due to *Vibrio Cholera* and *Escheriachia coli*. Drugs are commonly used in peptic ulcer disease to block or neutralize gastric acidity, (5), (6), although they are generally used without documenting the physiological effectiveness in the individual patient.

In the prior art, the measurement of gastric acid secretion has involved the placing of a tube in the stomach, and suctioning gastric contents for approximately two hours. Acid secretion is stimulated during this procedure with a subcutaneous injection of betazole or pentagastrin. Measurement of acid in the specimen is time consuming for the technician, and hence expensive. Because of the discomfort to the patient the need for careful specimen collection, the time involved and the expense, the test is rarely carried out except for hospitalized patients.

DESCRIPTION OF THE PRESENT INVENTION

Briefly stated, the invention comprises a non-invasive test for gastric acid secretion, which is suitable for use with outpatients or even at home. The test is suitable to screen patients for pernicious anemia, gastric carcinoma, Zollinger-Ellison syndrome, and even more usefully, it is useful in the documentation of the physiologic response to hydrogen blocking drugs such as cimetidine in order to adjust dosage for the drug.

We have developed an oral magnesium, breath and belch hydrogen test for gastric acidity. In this test, the subject takes an oral stimulus (such as betazole), and some thirty minutes later takes a capsule containing magnesium powder. If acid is present the magnesium reacts with the hydrochloric acid liberating hydrogen gas. Some of the hydrogen gas is absorbed into the circulation and appears in the breath, and some may be belched. The recovery of high levels of hydrogen correlates with the presence of large amounts of gastric acid.

The air samples (breath or belch) are collected using a simple device (e.g., a weather balloon), and can be stored in a plastic syringe or vacutainer tube for transport to a central laboratory. The concentration of hydrogen gas is easily measured using a gas chromatograph in less than two minutes time. In general, the test is performed as follows: the patients are fasted overnight before the test and the test is normally done in the morning. Base line measurements of breath hydrogen are obtained, then betazole is given. Thirty minutes later an oral capsule containing 150 mg. of magnesium powder (−150 mesh) is given. Collections of breath and belch samples continue for approximately 90 minutes and the total hydrogen recovery is calculated.

Initial safety testing was conducted in both rabbits and humans. Rabbits given oral magnesium and subcutaneous betazole showed no histologic changes of the gastric or intestinal mucosa, nor did the kidneys, liver or heart show any pathologic changes. Serum magnesium levels did not change.

Humans given betazole and magnesium were monitored for toxicity. They suffered no unexpected side effects, and had no gastrointestinal bleeding, and had no change in liver or kidney tests. The level of serum calcium and magnesium likewise did not change.

The inherent safety of the method being established, we proceeded with clinical testing. While similar tests could be developed for gastric acid based upon the reaction of a reducing metal (e.g., magnesium or zinc) with gastric acid to produce hydrogen gas, we chose magnesium because it reacts rapidly with hydrochloric acid and can safely be given orally. After the hydrogen gases are formed in the stomach, it is expected that a proportion would be absorbed, circulate to the lungs, and appear in exhaled air, while the remainder might be belched. We therefore developed a test to recover hydrogen gas from both of these sources.

Six volunteers underwent six tests each in a first series of experiments and five additional volunteers underwent four tests each in a second series of experiments. In each experiment the volunteers were fasted overnight before the test began at 9:00 A.M. and in each experiment baseline measurements of breath volumes and hydrogen concentrations were made. Differences between the first and second series of experiments were as follows: In the first series 30 or 60 second collections of exhaled air were made every five minutes throughout the test and belches were collected separately. In the second series of experiments the volunteers breathed continuously through the valve for the entire experiment; hence, the belches and breath were collected together. In both cases the exhaled air and belches were collected into a neoprene bag connected to the expiratory side of an inspiratory-expiratory valve by plastic tubing. A sampling valve in the bag permitted withdrawal of samples of collected air.

After collecting baseline samples for at least 15 minutes we administered betazole (Histalog, Lilly). In the first series of experiments we gave 50 mg. of histalog subcutaneously, but in the second series of experiments we gave 100 mg. betazole orally in 1. ml of tap water. 30 minutes later we administered finely ground magnesium metal (−50 mesh, Alpha Products, Danvers, Mass.) in a gelatin capsule with 1. ml water. We continued to collect exhaled air for at least 90 minutes following the magnesium.

We measured the volumes of the collected air using a Wet Test meter (Precision Scientific, Chicago, Ill.) or Dry Test meter, and measured the hydrogen concentration using a gas chromatograph (Quintron Microlyzer, Quintron Instruments, Milwaukee, Wis.). Volumes of hydrogen in exhaled air were converted in micromoles using the Ideal Gas Law. Breath hydrogen excretion rates (micromoles of hydrogen per minute) were calculated from each collection of exhaled air.

We estimated the amount of hydrogen in the exhaled air that was produced by the reaction of magnesium metal with stomach acid in each experiment by plotting post-magnesium breath hydrogen excretion rates against time and calculating the area between this curve and a horizontal line drawn two standard deviations above the mean of the basal (pre-magnesium) breath hydrogen excretion rates. This area defines the "excess breath hydrogen." Since, in preliminary experiments, betazole did not increase breath hydrogen excretion rates, all pre-magnesium collections of exhaled air were used to calculate the mean basal excretion rate. The amount of hydrogen in belches was calculated separately and the sum of the belched hydrogen plus excess breath hydrogen is the "total excess hydrogen" recovered.

A dose of 10 mg of magnesium was given in the first test. In subsequent tests, the dose was increased to 50, 100, 150 and 200 mg to determine the dose related response. Finally, to evaluate the effect of high gastric pH, we repeated the 150 mg dose without betazole but with oral cimetidine and bicarbonate to neutralize the acidity. For this final test we gave 300 mg of cimetidine the night before and 300 mg of cimetidine with 500 mg of sodium bicarbonate in 1. ml of water in place of the betazole (30 minutes before the magnesium was given).

No unexpected reactions were observed. All volunteers had symptoms consistent with betazole, e.g., flushing, headache and tachycardia. No one had abdominal cramps or dyspepsia, and all tests for occult fecal blood were negative. Serum values remained unchanged.

The mean (plus or minus S.D.) basal breath hydrogen excretion rate from all experiments was $2.5 \pm 2.7$ micromoles per minute. Increases in hydrogen recovery began to occur 10 to 25 minutes following the 150 mg dose of magnesium, but tended to be delayed up to 50 minutes with lower doses.

Total excess hydrogen increased linearly with increasing doses of magnesium up to the 150 mg dose. When the subjects were given cimetidine and bicarbonate, the amount of total excess hydrogen evolved was minimal.

In these studies we have demonstrated increases in hydrogen recovery in normal subjects following subcutaneous betazole and oral magnesium. Evidence that the response seen is specific for gastric acid includes the following: hydrogen recovery did not increase until magnesium was given so this increase was not a nonspecific effect of the betazole. Also, the amount of hydrogen recovered correlated directly with the magnesium dose up to 150 mg. The response was then blocked with cimetidine and bicarbonate, agents which inhibit gastric acid secretion and neutralize acid, respectively.

The apparent lesser response to 200 mg is not easily explained. One would expect a plateau in the dose response curve as the magnesium reached higher doses. The reason for the decrease in response is not known. Most of the subjects, however, had fewer side effects from the betazole, particularly less flushing, after repeated doses and it is possible that the subjects became tolerant with weekly doses of betazole.

As expected, the procedure as performed was entirely safe. In evaluating the potential hazards of giving oral magnesium we considered the possible toxic effects of the magnesium metal, of the magnesium ions formed from the reaction with HCl, and the reaction itself. Magnesium metal, being insoluble, is not absorbed, hence passes out with the stool. Magnesium ions can be absorbed as a nutrient. The recommended daily requirement of magnesium for an adult male is 350 mg (9) significantly greater than the largest administered dose. Much higher doses of magnesium are used in laxatives and antacids. Finally, the reaction is slightly exothermic; however, the small amount of heat generated is unlikely to cause damage to the gastric mucosa. The heat of reaction of magnesium metal with aqueous hydrogen ion is minus 110 kcal/mole. By comparison, the heat of reaction of $Mg(OH)_2$ (a common antacid) with aqueous hydrogen ion is 26.0 kcal/mole (calculated from standard heats of formation. The negative test for occult fecal blood is reassuring evidence that no significant mucosal injury occurred with the procedure. Likewise, tests of liver and kidney function and calcium and magnesium remained unchanged after magnesium ingestion. Previous studies in rabbits given repeated doses of magnesium metal by gastric tube revealed no abnormalities of stomach, intestine, kidney, liver or heart.

The following examples are illustrative of the wide utility offered by the present invention, and are not to be considered as exhaustive of useful possibilities.

EXAMPLE I

A middle-aged male patient complained of epigastric pain. Upon conducting an upper G.I. series (barium swallow), the presence of a gastric ulcer was obtained. To assist in differentiating between a benign and a malignant ulcer, the patient then underwent a magnesium-breath hydrogen test. Following betazole stimulation and oral magnesium, there was no increase in hydrogen excretion indicating that the patient's stomach was incapable of secreting acid (i.e., the patient had achlorhydria). Based upon this information, it was highly suspected that the patient had a gastric cancer, and plans were made for the biopsy and treatment of this condition.

EXAMPLE II

An elderly female patient complained of feeling of weakness. An examination found her to be anemic. During examination, a magnesium-breath hydrogen test demonstrated that the patient was suffering from achlorhydria. This test increased the likelihood of pernicious anemia, so that a chilling test was ordered to establish the diagnosis. If the breath hydrogen test had indicated normal levels of gastric acid, pernicious anemia would have been ruled out.

EXAMPLE III

A middle-aged male patient was under treatment for a duodenal ulcer with cimetidine, in the amount of 200 mg twice daily. He continued to have a burning epigastric pain. A magnesium-breath hydrogen test revealed that the patient continued to secrete normal amounts of gastric acid. The dosage of cimetidine was therefore increased to 300 mg three times daily. A repeat magnesium-breath hydrogen test was associated with only a slight increase in excess hydrogen, from which it was concluded that the acid production had been greatly decreased with the increased dose of cimetidine.

It will be appreciated that although the chemical agent used in the above disclosure to stimulate acid production was betazole, other stimuli are also suitable, such as pentagastrin, alcohol, or even a standard test meal.

It may thus be seen that we have developed a novel and highly useful method to measure gastric acid secretion in individual patients. Not only can the disclosed method be used to screen patients for diseases associated with abnormalities of gastric acid secretion, but the method may also be used for monitoring patients taking pharmacologic agents such as cimetidine designed to block production of gastric acid.

We wish it to be understood that we do not consider the invention limited to the precise details disclosed in the foregoing specification, for obvious modifications will occur to those skilled in the art to which the invention relates.

We claim:

1. A method of testing the breath and belches of a patient for the purpose of determining the degree of gastric acidity on an ephemeral basis comprising the steps of: collecting exhaled air and belches over a short time period; administering an acid production stimulant, and approximately 30 minutes thereafter from 10 to 200 mg of finely divided magnesium in encapsulated form; collecting exhaled air and belches for at least 90 minutes following the administration of magnesium; measuring the volume of collected air and the free hydrogen content thereof, and determining the hydrogen excretion rate per given unit of time for both pre-magnesium and post-magnesium breathing; determining the excess breath hydrogen rate over the pre-magnesium breath hydrogen rate; and using said excess breath hydrogen rate as an indication of the pH and acid secretion of the digestive system.

2. The method set forth in claim 1, in which the acid production stimulant is selected from the group consisting of betazole, pentagastrin, alcohol and a standard test meal.

* * * * *